US012576267B2

(12) United States Patent
Jenney et al.

(10) Patent No.: US 12,576,267 B2
(45) Date of Patent: Mar. 17, 2026

(54) TISSUE STIMULATION APPARATUS AND METHODS OF MAKING THE SAME

(71) Applicant: The Alfred E. Mann Foundation for Scientific Research, Valencia, CA (US)

(72) Inventors: Christopher Reed Jenney, Valencia, CA (US); Neil Talbot, La Crescenta, CA (US); Joseph L. Calderon, Santa Clarita, CA (US); Sahar Elyahoodayan, Los Angeles, CA (US); William Andrew Brandt, Castaic, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 407 days.

(21) Appl. No.: 18/186,927

(22) Filed: Mar. 20, 2023

(65) Prior Publication Data

US 2024/0009452 A1     Jan. 11, 2024

Related U.S. Application Data

(60) Provisional application No. 63/358,455, filed on Jul. 5, 2022.

(51) Int. Cl.
*A61N 1/05* (2006.01)

(52) U.S. Cl.
CPC .... *A61N 1/0556* (2013.01); *A61B 2562/0209* (2013.01)

(58) Field of Classification Search
CPC ...................... A61N 1/0556; A61B 2562/0209
See application file for complete search history.

(56) References Cited

U.S. PATENT DOCUMENTS

| | | | |
|---|---|---|---|
| 4,573,481 A | 3/1986 | Bullara | |
| 4,602,624 A | 7/1986 | Naples et al. | |
| 4,940,065 A | 7/1990 | Tanagho et al. | |
| 5,251,634 A | 10/1993 | Weinberg | |
| 5,400,784 A | 3/1995 | Durand et al. | |
| 5,439,485 A | 8/1995 | Mar et al. | |
| 5,487,756 A | 1/1996 | Kallesoe et al. | |
| 5,634,462 A | 6/1997 | Tyler et al. | |
| 5,919,220 A | 7/1999 | Stieglitz et al. | |
| 6,066,165 A | 5/2000 | Racz | |
| 6,093,197 A | 7/2000 | Bakula et al. | |

(Continued)

FOREIGN PATENT DOCUMENTS

| | | |
|---|---|---|
| CN | 112402786 A | 2/2021 |
| WO | WO 2008092246 A1 | 8/2008 |

(Continued)

OTHER PUBLICATIONS

U.S. Appl. No. 17/463,611, filed Sep. 1, 2021, 20220062629 A1.

(Continued)

*Primary Examiner* — Linda C Dvorak
*Assistant Examiner* — Abigail Bock
(74) *Attorney, Agent, or Firm* — Henricks Slavin LLP

(57) ABSTRACT

A method of forming a nerve cuff by combining a plurality of electrically conductive members with respective rear surfaces and grit blasted front surfaces with a nerve cuff body, which includes a respective plurality of windows, in such a manner that exposed portions of the grit blasted front surfaces are within the windows.

19 Claims, 5 Drawing Sheets

(56) References Cited

U.S. PATENT DOCUMENTS

| | | | |
|---|---|---|---|
| 6,210,339 B1 | 4/2001 | Kiepen et al. | |
| 6,292,703 B1 | 9/2001 | Meier et al. | |
| 7,383,090 B2 * | 6/2008 | O'Brien | A61N 1/05 |
| | | | 600/382 |
| 7,499,742 B2 | 3/2009 | Bolea et al. | |
| 7,794,256 B1 | 9/2010 | Sochor | |
| 7,809,442 B2 | 10/2010 | Bolea et al. | |
| 7,813,812 B2 | 10/2010 | Kieval et al. | |
| 7,996,092 B2 | 8/2011 | Mrva et al. | |
| 8,116,882 B2 | 2/2012 | Kowalczewski | |
| 8,155,757 B1 | 4/2012 | Neisz et al. | |
| 8,224,449 B2 | 7/2012 | Carbunaru et al. | |
| 8,311,645 B2 | 11/2012 | Bolea et al. | |
| 8,340,785 B2 | 12/2012 | Bonde et al. | |
| 8,660,665 B2 | 2/2014 | Walter et al. | |
| 8,792,973 B2 | 7/2014 | Moran et al. | |
| 8,934,992 B2 | 1/2015 | Johnson et al. | |
| 9,186,511 B2 * | 11/2015 | Bolea | A61N 1/3615 |
| 9,227,053 B2 | 1/2016 | Bonde et al. | |
| 9,486,628 B2 | 11/2016 | Christopherson et al. | |
| 9,549,708 B2 | 1/2017 | Mercanzini et al. | |
| 9,603,538 B2 | 3/2017 | Fisher et al. | |
| 9,849,288 B2 | 12/2017 | Meadows et al. | |
| 9,889,304 B2 | 2/2018 | Mercanzini | |
| 9,931,045 B2 | 4/2018 | Brunnett et al. | |
| 10,758,723 B2 | 9/2020 | Fang et al. | |
| 11,833,348 B2 | 12/2023 | Brandt et al. | |
| 12,194,290 B2 | 1/2025 | Dearden et al. | |
| 12,296,172 B2 | 5/2025 | Jenny et al. | |
| 12,350,489 B2 | 7/2025 | Jenny et al. | |
| 2002/0198582 A1 | 12/2002 | Edell et al. | |
| 2005/0070982 A1 | 3/2005 | Heruth et al. | |
| 2005/0186829 A1 | 8/2005 | Balsells | |
| 2006/0004430 A1 | 1/2006 | Rossing et al. | |
| 2006/0030919 A1 | 2/2006 | Mrva et al. | |
| 2007/0123765 A1 | 5/2007 | Hetke et al. | |
| 2007/0185542 A1 | 8/2007 | Bolea et al. | |
| 2008/0082137 A1 | 4/2008 | Kieval et al. | |
| 2008/0103545 A1 | 5/2008 | Bolea et al. | |
| 2008/0172101 A1 | 7/2008 | Bolea et al. | |
| 2009/0132042 A1 | 5/2009 | Hetke et al. | |
| 2009/0210042 A1 | 8/2009 | Kowalczewski | |
| 2010/0305674 A1 | 12/2010 | Zarembo et al. | |
| 2010/0331933 A1 | 12/2010 | Carbunaru et al. | |
| 2011/0066196 A1 | 3/2011 | Alexander et al. | |
| 2011/0130815 A1 * | 6/2011 | Gibson | B23K 26/40 |
| | | | 29/874 |
| 2011/0154655 A1 | 6/2011 | Hetke et al. | |
| 2011/0251473 A1 | 10/2011 | Moran et al. | |
| 2011/0301665 A1 | 12/2011 | Mercanzini et al. | |
| 2012/0089153 A1 | 4/2012 | Christopherson et al. | |
| 2012/0150255 A1 | 6/2012 | Lindenthaler et al. | |
| 2012/0154256 A1 | 6/2012 | Grover et al. | |
| 2012/0277819 A1 | 11/2012 | Cowley et al. | |
| 2012/0316417 A1 | 12/2012 | Vetter | |
| 2013/0030352 A1 | 1/2013 | Seymour et al. | |
| 2013/0085361 A1 | 4/2013 | Mercanzini et al. | |
| 2013/0090711 A1 | 4/2013 | Ramachandran et al. | |
| 2013/0150938 A1 | 6/2013 | Carbunaru et al. | |
| 2013/0304174 A1 | 11/2013 | Langhals et al. | |
| 2014/0005763 A1 | 1/2014 | Cederna et al. | |
| 2014/0058482 A1 | 2/2014 | Gupta et al. | |
| 2014/0163659 A1 | 6/2014 | Boling | |
| 2014/0188202 A1 | 7/2014 | Zarembo et al. | |
| 2014/0228905 A1 | 8/2014 | Bolea | |
| 2014/0303703 A1 | 10/2014 | Mercanzini et al. | |
| 2015/0119673 A1 | 4/2015 | Pellinen et al. | |
| 2015/0128413 A1 | 5/2015 | Vetter et al. | |
| 2015/0157854 A1 | 6/2015 | Hetke et al. | |
| 2015/0174396 A1 | 6/2015 | Fisher et al. | |
| 2015/0224307 A1 | 8/2015 | Bolea | |
| 2015/0374975 A1 | 12/2015 | Callegari et al. | |
| 2016/0184581 A1 | 6/2016 | Bonde et al. | |
| 2016/0199367 A1 * | 7/2016 | Jo | A61K 31/122 |
| | | | 514/288 |
| 2016/0199637 A1 | 7/2016 | Xu et al. | |
| 2016/0287863 A1 | 10/2016 | Mercanzini et al. | |
| 2016/0331326 A1 | 11/2016 | Xiang et al. | |
| 2016/0331994 A1 | 11/2016 | Smith et al. | |
| 2017/0021163 A1 | 1/2017 | Westlund et al. | |
| 2017/0225004 A1 | 8/2017 | Casse et al. | |
| 2017/0266436 A1 | 9/2017 | Suwito et al. | |
| 2017/0319846 A1 | 11/2017 | Plachta et al. | |
| 2018/0117313 A1 | 5/2018 | Schmidt et al. | |
| 2018/0132790 A1 | 5/2018 | Yao et al. | |
| 2018/0221660 A1 | 8/2018 | Suri et al. | |
| 2018/0318577 A1 | 11/2018 | Ng et al. | |
| 2018/0318578 A1 | 11/2018 | Ng et al. | |
| 2019/0060646 A1 | 2/2019 | Ng et al. | |
| 2019/0069949 A1 | 3/2019 | Vrba et al. | |
| 2019/0282805 A1 | 9/2019 | Schmidt et al. | |
| 2020/0069935 A1 | 3/2020 | Johnson et al. | |
| 2020/0083922 A1 | 3/2020 | Hong et al. | |
| 2020/0146583 A1 | 5/2020 | Hestad et al. | |
| 2020/0230412 A1 | 7/2020 | Rondoni et al. | |
| 2020/0230421 A1 | 7/2020 | Zaidi et al. | |
| 2020/0306526 A1 | 10/2020 | Doguet et al. | |
| 2021/0085964 A1 | 3/2021 | Zaidi et al. | |
| 2021/0205662 A1 | 7/2021 | Lu et al. | |
| 2022/0062629 A1 | 3/2022 | Dearden | |
| 2022/0088374 A1 * | 3/2022 | Ackermann | A61N 1/40 |
| 2022/0184387 A1 | 6/2022 | Searfoss et al. | |
| 2022/0313987 A1 | 10/2022 | Jenny et al. | |
| 2023/0010510 A1 | 1/2023 | Brandt et al. | |
| 2023/0241394 A1 | 8/2023 | Jenny et al. | |
| 2024/0058602 A1 | 2/2024 | Brandt et al. | |
| 2024/0108883 A1 | 4/2024 | Trivedi et al. | |
| 2025/0121182 A1 | 4/2025 | Dearden et al. | |
| 2025/0182934 A1 | 6/2025 | Jenny et al. | |
| 2025/0205478 A1 | 6/2025 | Jenny et al. | |
| 2025/0256093 A1 | 8/2025 | Jenny | |
| 2025/0276174 A1 | 9/2025 | Jenny | |
| 2025/0303146 A1 | 10/2025 | Jenny et al. | |

FOREIGN PATENT DOCUMENTS

| | | |
|---|---|---|
| WO | WO 2009045772 A1 | 4/2009 |
| WO | WO 2012154256 A1 | 11/2012 |
| WO | WO 2013188871 A1 | 12/2013 |
| WO | WO 2016039768 A1 | 3/2016 |
| WO | WO 2020182293 A1 | 9/2020 |
| WO | WO 2021108810 A1 | 6/2021 |

OTHER PUBLICATIONS

U.S. Appl. No. 17/463,630, filed Sep. 1, 2021, 20230010510 A1.
U.S. Appl. No. 17/683,598, filed Mar. 1, 2022, 20220313987 A1.
U.S. Appl. No. 17/710,570, filed Mar. 31, 2022.
U.S. Appl. No. 18/186,927, filed Mar. 20, 2023.
PCT Search Report and Written Opinion dated Jun. 16, 2023 for PCT App. Ser. No. PCT/US023/064730.
U.S. Appl. No. 17/463,630, filed Sep. 1, 2021, U.S. Pat. No. 11,833,348 B2.
U.S. Appl. No. 18/495,503, filed Oct. 26, 2023, 20240058602 A1.
U.S. Appl. No. 17/710,570, filed Mar. 31, 2022, 20230241394 A1.
U.S. Appl. No. 18/468,730, filed Sep. 17, 2023, 20240108883 A1.
U.S. Appl. No. 18/186,927, filed Mar. 20, 2023, 20240009452 A1.
U.S. Appl. No. 19/019,360, filed Jan. 13, 2025.
U.S. Appl. No. 18/939,479, filed Nov. 6, 2024.
U.S. Appl. No. 18/985,448, filed Dec. 18, 2024.
U.S. Appl. No. 19/034,472, filed Jan. 22, 2025.
U.S. Appl. No. 18/495,503, filed Oct. 26, 2023.
U.S. Appl. No. 18/468,730, filed Sep. 17, 2023.
Brummer et al., "Electrical Stimulation with Pt Electrodes: I. A Method for Determination of "Real" Electrode Areas," IEEE Transactions on Biomedical Engineering, vol. BME-24, No. 5, pp. 436-439, Sep. 1977.
Rose et al., "Electrical Stimulation with Pt Electrodes: VIII. Electrochemically Safe Charge Injection Limits with 0.2 ms Pulses,"

(56)                    References Cited

OTHER PUBLICATIONS

IEEE Transactions on Biomedical Engineering, vol. 37, No. 11, pp.
1118-1120, Nov. 1990.

* cited by examiner

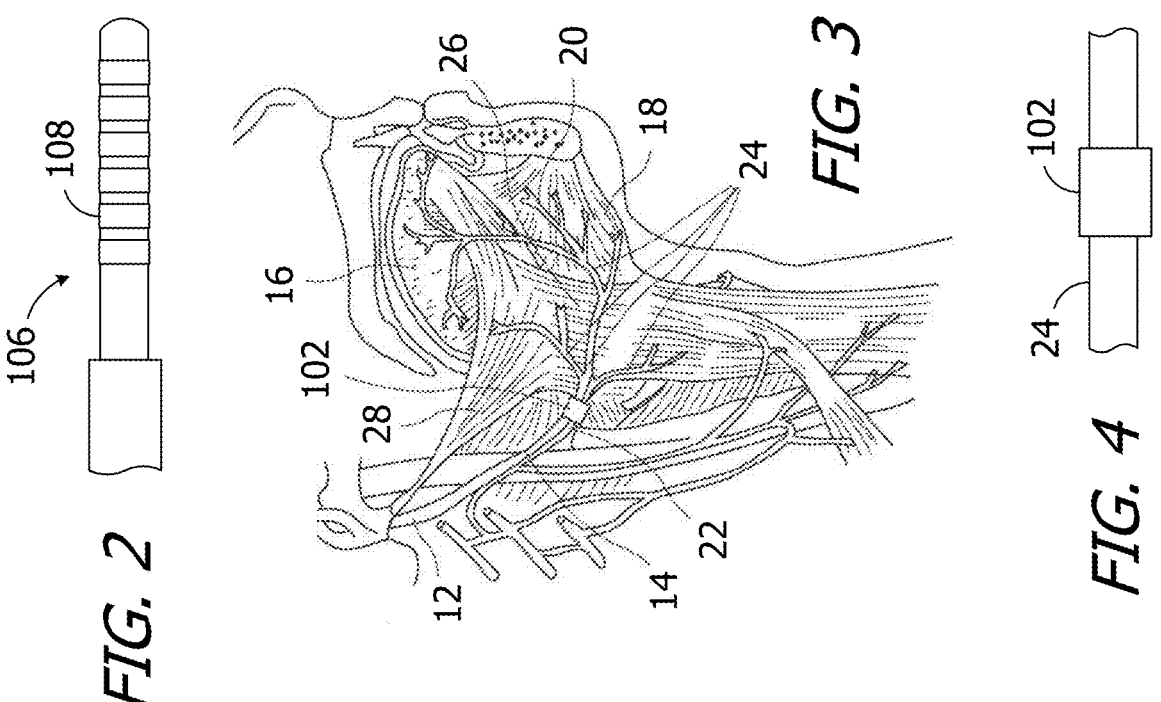
*FIG. 2*
*FIG. 3*
*FIG. 4*
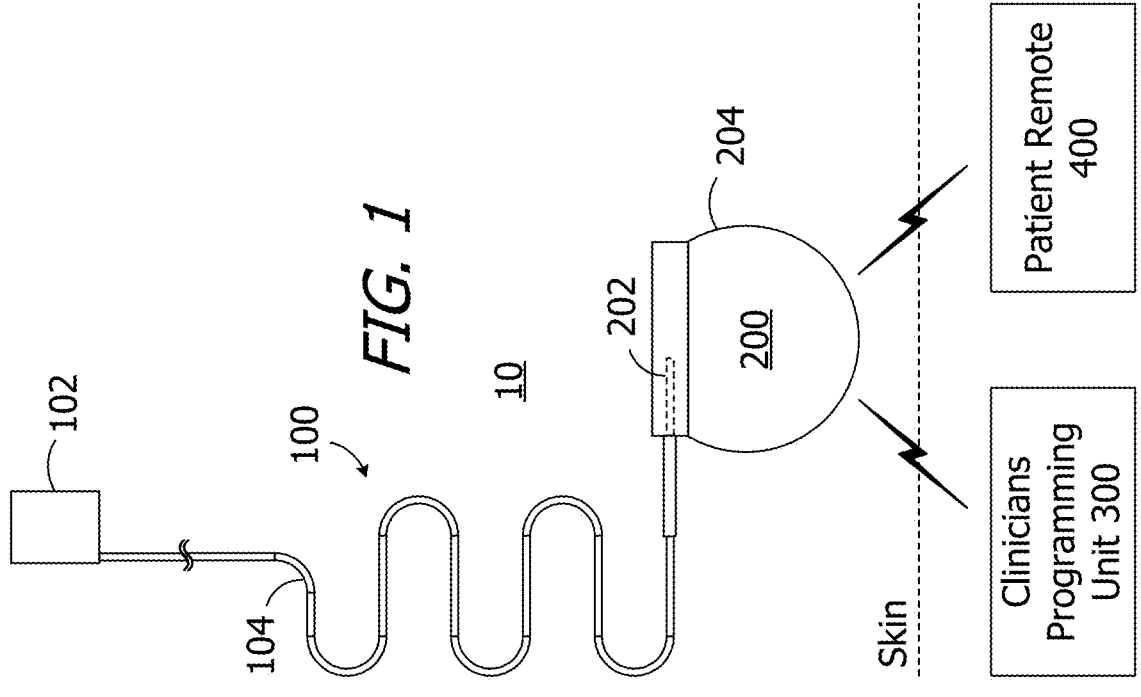
*FIG. 1*

TISSUE STIMULATION APPARATUS AND METHODS OF MAKING THE SAME

CROSS-REFERENCE TO RELATED APPLICATION

This application claims the benefit of U.S. Provisional Application No. 63/358,455, filed Jul. 5, 2022, and entitled "Grit Blasting Of Electrodes To Improve Mechanical and Electrical Performance," which is incorporated herein by reference.

BACKGROUND OF THE INVENTIONS

1. Field of Inventions

The present inventions relate generally to tissue stimulation apparatus and method of making the same.

2. Description of the Related Art

There are many instances where tissue is stimulated to produce a desired therapeutic result. Although the present inventions are not limited to particular stimulation apparatus, one exemplary type of stimulation apparatus is an electrode lead that is used to stimulate the nerve fascicles of the hypoglossal nerve (HGN) to treat obstructive sleep apnea (OSA) and the present inventions are described in this exemplary context. OSA is a highly prevalent sleep disorder that is caused by the collapse of or increase in the resistance of the pharyngeal airway, often resulting from tongue obstruction.

Some proposed methods of alleviating apneic events involve the use of neurostimulators to open the upper airway. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during the inspiration portion of the respiratory cycle. In some instances, the trunk of the HGN is stimulated with a nerve cuff, including a cuff body and a plurality of electrically conductive contacts (sometimes referred to as "electrodes") on the cuff body, that is positioned around the HGN trunk. To that end, some nerve cuffs are pre-shaped to a furled state, may assume slightly less furled states, and may be unfurled to a flattened state. The HGN trunk nerve cuff may be configured in such a manner that it can be used to selectively stimulate nerve fascicles which innervate muscles that extend the tongue, while avoiding other nerve fascicles, with what is predominantly radial vector stimulation. Stimulation energy is supplied by way of cables that are connected to the electrically conductive contacts. HGN branches may also be stimulated. For example, an HGN GM branch may be stimulated with what is predominantly axial vector stimulation.

The contacts of at least some nerve cuffs are defined by electrically conductive members that are located between two non-conductive layers, i.e., a relatively thin front layer and a relatively thick rear layer, with the front layer including openings (or "windows") that expose portions of the conductive members. The portions of window-containing layer that cover the remainders of the conductive members, and that border the windows, are referred to herein as "window frames." The conductive members are connected by cables to stimulation circuitry. Exemplary nerve cuffs are illustrated and described in U.S. Pat. Pub. Nos. 2018/0318577A1, 2018/0318578A1, 2019/0060646A1, 2019/

0282805A1 and 2022/0313987A1, which are incorporated herein by reference in their entirety.

SUMMARY

The present inventors have determined that stimulation apparatus, such as nerve cuffs, are susceptible to improvement. For example, the present inventors have determined that certain electrically conductive materials with otherwise desirable properties (e.g., platinum-iridium) do not bond well with non-conductive materials that have desirable mechanical properties (e.g., silicone) or, when employed, the adhesive (e.g., silicone adhesive) that is used to bond non-conductive layers that are formed from materials that have desirable mechanical properties. The less than optimal bond, coupled with the thinness of the window frames and the stress that is applied to the conductive members when the nerve cuff is in manipulated (e.g., furled, unfurled, or twisted), may cause delamination of the nerve cuff at the window frames, exposure of internal components not intended for direct bodily fluid contact and, in some instances, dislodgement of the conductive members. Exposure of the internal components to bodily fluid may result in, for example, electrochemically driven oxidation of the cables during stimulation pulses and an increased risk of galvanic corrosion between the conductive member and cable materials in the crimp joints connecting the cables to the conductive members. In addition, exposure of the normally completely covered rear side of the conductive members to bodily fluid reduces the effective charge density which can result in less effective stimulation. Accordingly, the present inventors have determined that it would be desirable to provide nerve cuffs that, among other things, reduce the likelihood of delamination at the window frames.

Other issues identified by the present inventors are associated with the effective surface area of conventional flat electrodes, i.e., the surface area value that takes into account the surface roughness of the electrodes as well as the geometric boundaries defined by the windows. In particular, the present inventors have determined that it would be desirable to increase the effective surface area of flat electrodes without increasing window size in order to increase the amount of stimulation energy that can be safely delivered and to also reduce electrode-electrolyte impedance, thereby reducing power consumption by the stimulation circuitry.

A method in accordance with at least one of the present inventions includes forming a nerve cuff by combining a plurality of electrically conductive members with respective rear surfaces and grit blasted front surfaces with a nerve cuff body, which includes a respective plurality of windows, in such a manner that exposed portions of the grit blasted front surfaces are within the windows.

A method in accordance with at least one of the present inventions includes grit blasting conductive material using first grit blasting parameters to form a grit blasted conductive surface, assembling a nerve cuff that includes a cuff body having a plurality of windows and the grit basted conductive material positioned such that portions of the grit blasted conductive material are located within the windows, and removing contaminants from the conductive material located within the windows of the assembled nerve cuff by grit blasting the conductive material located within the windows using second grit blasting parameters that are different than the first grit blasting parameters An electrode lead in accordance with at least one of the present inventions includes an elongate lead body, a biologically compatible, elastic, electrically insulative body affixed to the distal end of the lead body including a rear later and a front layer with a plurality of windows that define respective perimeters and areas defined by the perimeters ("AWs"), a plurality of electrically conductive members located between the front and rear layers of the electrically insulative body, each electrically conductive member defining a front surface, a rear surface and an outer perimeter, and being aligned with a respective window in such a manner that the windows are located inwardly of the outer perimeters thereby defining front surface exposed portions with respective effective surface areas ("EPESAs"), and a plurality of electrical conductors extending through the lead body from at least some of the electrically conductive members to the proximal end of the lead body, wherein EPESA to AW ratios of at least 2.0 are defined at the front surfaces of the electrically conductive members. The present inventions also include systems with an implantable pulse generator or other implantable stimulation device in combination with such an electrode lead.

BRIEF DESCRIPTION OF THE DRAWINGS

Detailed descriptions of exemplary embodiments will be made with reference to the accompanying drawings.

FIG. 1 is a plan view of a stimulation system in accordance with one embodiment of a present invention.

FIG. 2 is a plan view of a portion of the stimulation system illustrated in FIG. 1.

FIG. 3 is a cut-away anatomical drawing of the head and neck area illustrating the muscles that control movement of the tongue, the HGN and its branches that innervate these muscles, and the nerve cuff illustrated in FIG. 1 on the HGN trunk.

FIG. 4 is a plan view showing the nerve cuff illustrated in FIG. 1 on the HGN GM branch.

DETAILED DESCRIPTION OF THE EXEMPLARY EMBODIMENTS

Figures 5, 6, 7:
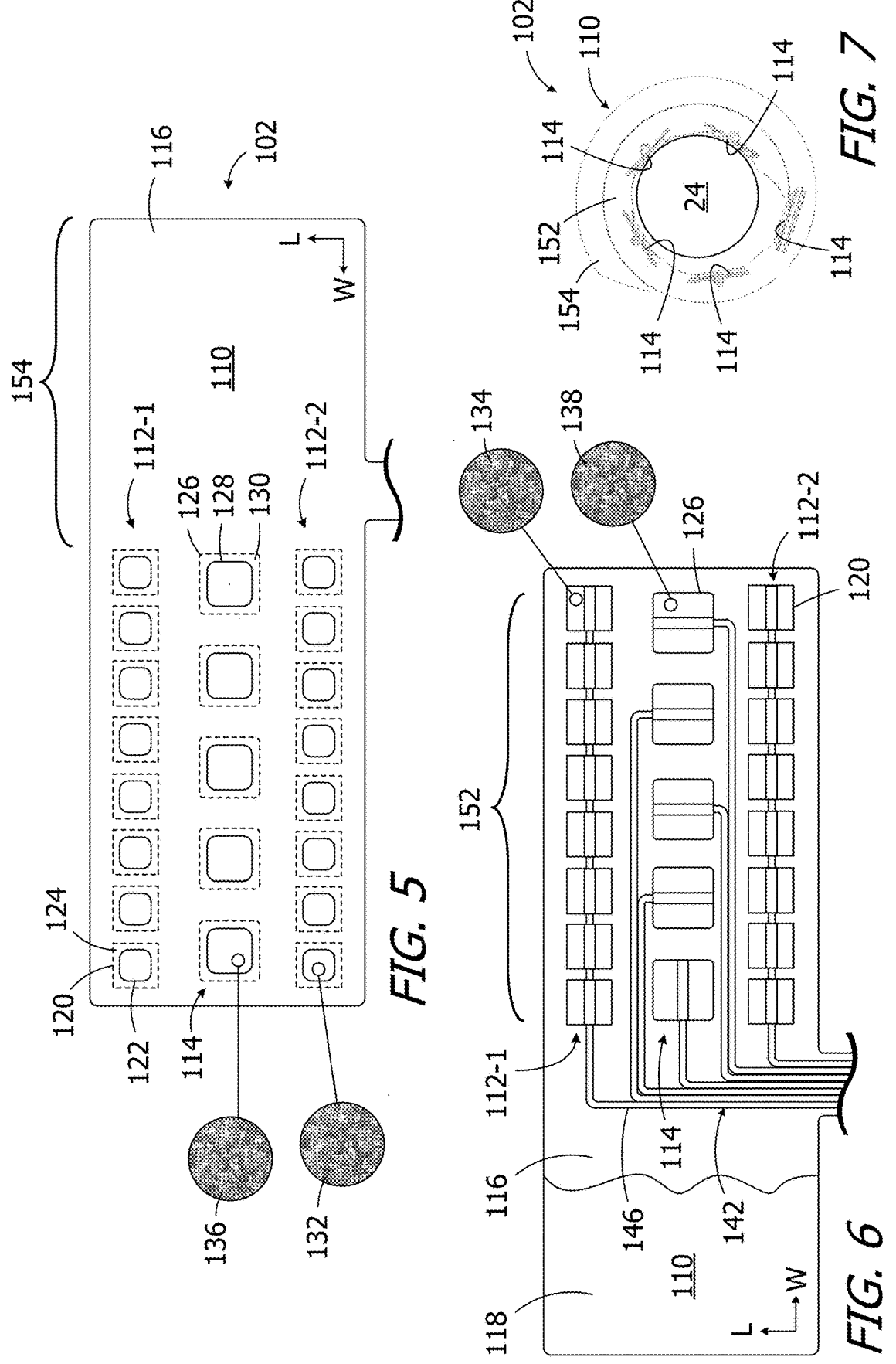
FIG. 5 is a front view of the nerve cuff illustrated in FIG. 1 in an unfurled state.
FIG. 6 is a rear, cutaway view of the nerve cuff illustrated in FIG. 1 in an unfurled state.
FIG. 7 is a section view of the nerve cuff illustrated in FIG. 1 in a furled state around a HGN branch.

The following is a detailed description of the best presently known modes of carrying out the inventions. This description is not to be taken in a limiting sense, but is made merely for the purpose of illustrating the general principles of the inventions.

Referring to FIGS. 1 and 2, a stimulation system 10 in accordance with one embodiment of a present invention includes an electrode lead 100 and an implantable stimulator such as the implantable pulse generator ("IPG") 200. A clinician's programming unit 300, a patient remote 400 and/or an IPG charger (not shown) may also be provided in some instances. Suitable IPGs, clinician's programming units and patient remotes are described, for example, in U.S. Pat. Pub. No. 2022/0313987A1. The exemplary electrode lead 100 includes a nerve cuff 102 and a lead body 104 that couples the nerve cuff 102 to the IPG 200 by way of lead connector 106, with a plurality contacts 108, on the proximal end of the lead body 104 and a corresponding connector receptacle 202 on the IPG 200. The nerve cuff 102 is configured in such a manner that it may be circumferentially disposed around either the HGN trunk or a HGN branch (e.g., the HGN GM branch) as is discussed below with reference to FIGS. 3 and 4. The lead body 104 may include one or more S-shaped sections in order to provide strain relief (as shown) or may be straight. The S-shaped sections accommodate body movement at the location within the neck where the lead body 104 is implanted, thereby reducing the likelihood that the HGN will be damaged due to unavoidable pulling of the electrode lead 100 that may result from neck movements. The accommodation provided by the S-shaped sections also reduces the likelihood of fatigue damage. Additionally, although the exemplary system 10 includes a single electrode lead 100, other embodiments may include a pair of electrode leads 100 for bilateral HGN stimulation and an IPG (not shown) with two connector receptacles.

Turning to FIG. 3, and as alluded to above, the nerve cuff 102 may be positioned around the trunk 14 of the HGN 12 and used to stimulate the muscles that anteriorly move the tongue 16 and, in particular, the fascicles of the HGN 12 that innervate the tongue protrusor muscles, such as the genioglossus 18 and/or the geniohyoid muscles 20. The nerve cuff 102 is positioned on the HGN trunk 14 at a position 22 proximal to the HGN branches 24. Although there are advantages to implanting the nerve cuff 102 at this proximal position 22, i.e., reduced surgical time and effort as well as reduced risk and trauma to the patient, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16. Accordingly, while some clinicians may desire to stimulate the HGN 12 at the HGN trunk 14, others may desire to stimulate the HGN at the GM branch 24. As illustrated in FIG. 4, the same nerve cuff 102 is configured in such a manner that it may be positioned the HGN GM branch 24 instead of the trunk 14.

The exemplary nerve cuff 102 is shown in a flattened, unfurled state in FIGS. 5 and 6 and is shown in a furled (or "curled") state in FIG. 7. In the illustrated implementation, the nerve cuff 102 is pre-set (or "pre-shaped") to the furled state and an external force may be used to partially or completely unfurl the nerve cuff 102. The nerve cuff 102 will return to the pre-shaped furled state when the force is removed and, as discussed below, may assume a variety furled states depending on the size of the HGN trunk or HGN branch that the nerve cuff 102 is placed around. Various examples of nerve cuffs that are capable of assuming different sizes are disclosed in aforementioned U.S. Pat. Pub. No. 2019/0060646A1.

The exemplary nerve cuff 102 illustrated in FIGS. 5-7 includes a cuff body 110 that defines a length L and a width W that is greater than the length, first and second pluralities of electrically conductive contacts (or "contacts") 112-1 and 112-2 on the cuff body 110, and a plurality of electrically conductive contacts (or "contacts") 114. The contacts 112-1 are spaced from one another in the length direction, as are the contacts 112-2. Contacts 112-1, 112-2 and 114 may also be referred to as "electrodes." The contacts 112-1 are connected to one another in series and function as a single relatively wide contact. The contacts 112-2 are also connected to one another in series and function as a single relatively wide contact. The contacts 114 are not connected to one another in series and, as compared to the each of the pluralities of contacts 112-1 and 112-2, the contacts 114 are relatively narrow. Although the number may increase or decrease in the context of other nerve applications, at least five contacts 114 may be spaced from one another in the width direction and located between the electrically conductive contacts 112-1 and 112-2 (collectively "contacts 112"), and there are five relatively narrow contacts 114 in the illustrated embodiment. As used herein, "relatively wide" structures are structures that are longer in the width direction than structures that are referred to as "relatively narrow" and "relatively narrow" structures are structures that are shorter in the width direction than structures that are referred to as "relatively wide."

In the implementation illustrated in FIGS. 5-7, the contacts 114 are centered relative to the contacts 112-1 and 112-2 and are aligned with one another in the length direction. In other implementations, the contacts may be non-centered relative to the relatively wide contacts 112-1 and 112-2 and/or offset from one another in the length direction. With respect to shape, and although the present inventions are not so limited, the individual contacts 112 are in the shape of rectangles with rounded corners, while the contacts 114 are squares with rounded corners. Other exemplary shapes are discussed below.

The cuff body 110 in the exemplary implementation may include a front layer 116 that will face the HGN trunk or branch and a rear layer 118 that will face away from the HGN trunk or branch. A plurality of conductive members 120, which form the contacts 112, are located between the front layer 116 and rear layer 118. The plurality of conductive members 120 are exposed by way of a plurality of windows 122 in the cuff body front layer 116. As discussed in greater detail below, the windows 122 are located inwardly of the outer perimeter (and outer edges) of the conductive members 120, which are shown in dashed lines in FIG. 5, and the exposed portions of the conductive members define the contacts 112. The portions of the front layer 116 that are located between the windows 122 and the outer perimeters (and outer edges) of the conductive members 120 define window frames 124 that hold the conductive members 120 against the rear layer 118 and between front and rear layers 116 and 118. Similarly, a plurality of conductive members 126, which form the contacts 114, are located between the front layer 116 and rear layer 118. The plurality of conductive members 126 are exposed by way of a plurality of windows 128 in the cuff body front layer 116. The windows 128 are located inwardly of the outer perimeter of the conductive members 126, which are shown in dashed lines in FIG. 5, and the exposed portions of the conductive members define the contacts 114. The portions of the front layer 116 that are located between the windows 128 and the outer perimeters (and outer edges) of the conductive members 126 define window frames 130 that hold the conductive members 126 against the rear layer 118 and between the front and rear layers 116 and 118.

The conductive members 120 each have a front surface 132 and a rear surface 134, while the conductive members 126 each have a front surface 136 and a rear surface 138. The front surfaces 132 and 136 face the nerve and have portions that are covered by the window frames 124 and 130 as well as portions that are exposed by the windows 122 and 128, while the rear surfaces 134 and 138 are covered by the rear layer 118. The front surfaces 132 and 136 have an effective surface area ("ESA") that is at least twice the area defined by the outer perimeters ("AP") of the associated conductive members 120 and 126. In at least some instances, including the illustrated embodiment, the rear surfaces 134 and 138 also have an ESA that is at least twice the AP of the associated conductive members 120 and 126. Put another way, the ESA to AP ratio is greater than that of conventional conductive members and is at least 2.0 in the exemplary implementations. For example, the ESA to AP ratio of the front and rear surfaces in other implementations may be at least 3.0, or at least 4.0, or at least 5.0, or at least 6.0, or at least 7.0, or at least 8.0, or at least 9.0, or at least 10.0. Additionally, the portions of the front surfaces 132 and 136 that are exposed by the windows 122 and 128 have an effective surface area ("EPESA") that is at least twice the area defined by the perimeters of the windows ("AW"). Put another way the EPESA to AW ratio is greater than that of conventional conductive member and window combinations and is at least 2.0 in the exemplary implementations. For example, the EPESA to AW ratio in other implementations may be at least 3.0, or at least 4.0, or at least 5.0, or at least 6.0, or at least 7.0, or at least 8.0, or at least 9.0, or at least 10.0.

One way to quantify the effective surface area of a surface is the average roughness (Ra) of that surface. The average roughness of the front surfaces 132 and 136 of conductive members 120 and 126 may be within a range of 100 nm to 800 nm in some implementations, may be within a range of 400 nm to 700 nm in other implementations, may be within a range of 500 nm to 600 nm in other implementations, and may be 566 nm in one specific implementation. For purposes of comparison, platinum-iridium foil may have a surface roughness of about 28 nm prior to a surface roughening process such as that described below.

In at least some instances, and as discussed in greater detail below with reference to FIGS. 10-15, the conductive member surfaces (and/or the conductive materials used to produce the conductive members) may be grit blasted or otherwise processed to increase the surface roughness and the effective surface area of the conductive material from its pre-processed state to achieve the desired ESA to AP and EPESA to AW ratios.

There are a number of advantages associated with an ESA to AP ratio that is greater than that of conventional conductive members and, for example, is at least 2.0. For example, as compared to an otherwise identical nerve cuff with conventional conductive members the stress applied to the conductive members 120 and 126 when the nerve cuff 102 is handled or is in a furled state will be less likely to cause delamination at the relatively thin window frames 124 and 130 and/or dislodgement of the conductive members and/or bodily fluid ingress that could reach facilitates increases in the amount of stimulation energy that can be safely delivered through a window of a given size (i.e., higher current density) at a given or lower voltage and to also reduces electrode-electrolyte impedance, thereby reducing power consumption by the stimulation circuitry and increasing IPG battery life, and increased electrode capacitance. It should also be noted that reducing electrode voltage reduces the likelihood of irreversible electrode reactions, such as electrolysis, which may lead to tissue irritation and/or damage. Increasing the effective surface area of the conductive members also reduces edge effects, i.e., high current densities at the electrode edges, and the corrosion and/or tissue damage associated therewith.

The contacts 112 and 114 in the illustrated embodiment may be individually electrically connected to the plurality contacts 108 on the lead connector 106 (FIG. 2) by wires or cables 142 (FIG. 6) that extend through the lead body 104. Each wire 142 includes a conductor 144 (FIG. 8), such as a conductor formed from MP35N material, and an insulator 146 (FIG. 6). The conductors may be connected to the rear side of the conductive members 120 and 126 by any suitable process. For example, and referring to FIGS. 8 and 9, each of the conductive members 120 (and 126) of the contacts 112 (and 114) may be formed from a tubular workpieces 148 that have been processed in the manner described below with reference to FIGS. 10-13 and that is crimped to a conductor as the tubular workpiece is compressed into a flat conductive member. Crimp tubes 150 may be provided at appropriate locations along the wires 142. The portions of the insulators 146 within the crimp tubes 150 may be removed prior to crimping (as shown) or simply squeezed out of the resulting joint during the crimping processes that form the conductive members 120 (and 126).

As is also illustrated in FIGS. 5-7, the cuff body 110 in the exemplary implementation includes a stimulation region 152 and a compression region 154. The contacts 112 and 114 are located within the stimulation region 152 and there are no contacts located within the compression region 154. The compression region 154 wraps around at least a portion of the stimulation region 152 when the nerve cuff 102 is in the pre-shaped furled state as well as in slightly larger, expanded and less tightly furled states, thereby resisting (but not preventing) expansion of the stimulation region and improving the electrical connection between the contacts 112 and 114 and the HGN. As a result, the exemplary nerve cuff 102 may be positioned around an HGN branch 24, as shown in FIG. 7, or the HGN trunk.

The exemplary cuff body 110 may be formed from any suitable material. Such materials may be biologically compatible, electrically insulative, elastic and capable of functioning in the manner described herein. The cuff materials should be pliable enough to allow a clinician to unfurl the cuff body 110 (and nerve cuff 102) and place the nerve cuff around the HGN trunk (or HGN GM branch). The exemplary materials should also be resilient enough to cause the nerve cuff body 110 (and nerve cuff 102) return to its pre-shaped furled state when the force is removed, yet flexible enough to allow the cuff body 110 (and nerve cuff 102) to instead assume the slightly larger, expanded and less tightly furled states, By way of example, but not limitation, suitable cuff body materials include silicone, polyurethane and styrene-isobutylene-styrene (SIBS) elastomers. Suitable materials for the contacts 112 and 114 include, but are not limited to, platinum-iridium and palladium.

During one exemplary manufacturing process, the front layer 116 with the windows 122 and 128 is formed in a mold from silicone or other cuff body material. The conductive members 120 and 126, which have been previously grit blasted or otherwise processed and connected to the wires 142, are placed into the mold over the front layer 116 with the conductive members aligned with the windows 122 and 128. The rear layer 118 is then formed in the mold from silicone or other cuff body material over the front layer 116, the conductive members 120 and 136, and portions of the wires 136. Primer may also be employed to improve adhesion and further reduce the likelihood of delamination as the nerve cuff is manipulated. For example, silicone primer may be applied to the front surfaces 132 and 136 of the conductive members 124 and 126 in the area of the window frames 124 and 130, as well to the rear surfaces 134 and 138, as is discussed in greater detail below with reference to FIGS. 16-19.

Figures 8, 9, 10, 11, 12, 13:
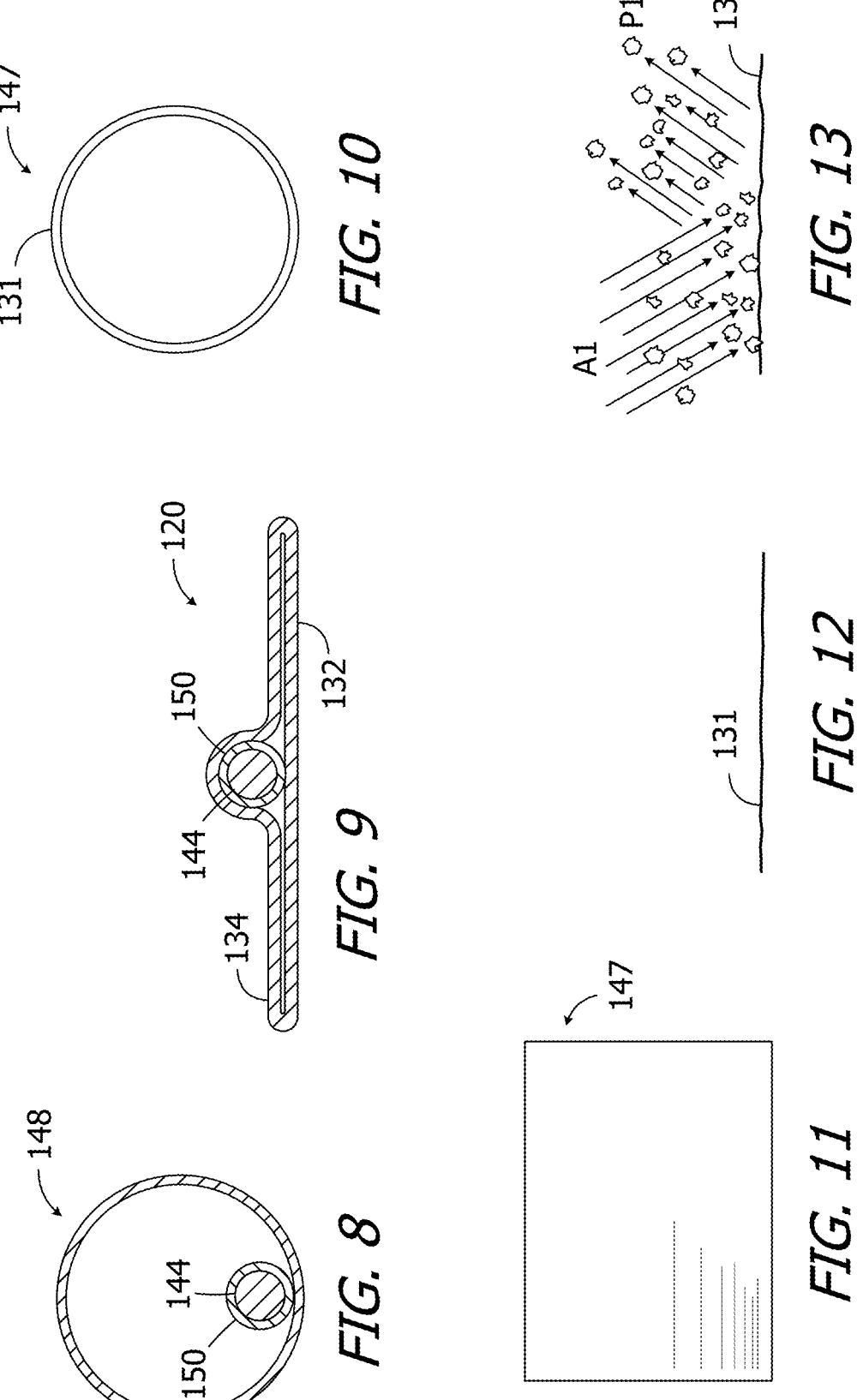
FIG. 8 is a section of a grit-blasted tubular workpiece, a crimp tube and a lead wire in accordance with one embodiment of a present invention.
FIG. 9 is a section view of a grit-blasted conductive member in accordance with one embodiment of a present invention.
FIG. 10 is an end view of a tubular workpiece in accordance with one embodiment of a present invention prior to undergoing a pre-assembly grit blasting process.
FIG. 11 is a top view of the tubular workpiece illustrated in FIG. 10 prior to undergoing a pre-assembly grit blasting process.
FIG. 12 is a magnified side view of the outer surface of the tubular workpiece illustrated in FIG. 10 prior to undergoing a pre-assembly grit blasting process.
FIG. 13 is a magnified side view of the outer surface of the tubular workpiece illustrated in FIG. 10 undergoing a pre-assembly grit blasting process.

As alluded to above, the present conductive members may be formed from a tubular workpiece that is processed in such a manner that the effective surface area is increased. To that end, and referring to FIGS. 10-12, the pre-processing tubular workpiece 147 is formed from platinum-iridium and has a relatively smooth, visually shiny outer surface 131 that will define the outer surfaces of the conductive member formed from the workpiece post-processing. FIG. 12 is a magnified representation of the outer surface 131. The outer surface 131 may be roughened by grit blasting or another suitable roughening process. Turning to FIG. 13, and as used herein, "grit blasting" is the shooting of a stream of small particulates P1 at a surface in a jet of air A1 and may be used to alter or clean the surface. The grit blasting transforms the pre-processing tubular workpiece 147, where the outer surface 131 has a relatively smooth, shiny state, to the post-processing tubular workpiece 148 illustrated in FIGS. 14 and 15, where the outer surface 131' has a finely textured, visually matte state and has an ESA to AP ratio of at least 2.0. The outer surface 131' may be transformed to the finely textured, visually matte state in a single grit blasting process. The post-processing tubular workpiece 148 may then be compressed into a conductive member 120 (or 126) in the manner described above with reference to FIGS. 8 and 9. In other instances, the grit blasting process may occur after the relatively flat conductive member is formed and prior to assembly of the associated nerve cuff. In either instance, the conductive members 120 and 126 may be incorporated into nerve cuffs with EPESA to AW ratios that are at least 2.0 as described above.

Grit blasting parameters such as air pressure, the material from which the particles are formed, size and size distribution, particle feed rate, particle shape, nozzle orifice diameter, air pressure, working distance and/or length of blasting time, may be selected and optimized to achieve the intended result.

One exemplary particle material is sodium bicarbonate. Sodium bicarbonate is advantageously both water soluble, which allows any residue from the grit blasting process to be easily removed with an aqueous cleaning process, and biocompatible. Other exemplary water soluble materials include potassium salt, sodium salt, carbonates, potassium, phosphates of sodium or potassium. By way of example, but not limitation, particle sizes in some implementations may range from up to about 50 μm to up to about 200 μm. Put another way, the particles in a particular process that are up to about 50 μm include particles that are 50 μm and other particles that are less than 50 μm. In some instances, particles 50 μm and below may be provided in a single quantity so that the surface being processed is struck with particles of various sizes in a single treatment, while in other instances multiple quantities of successive smaller particles may be employed in multiple treatments.

In one specific example that may be used to transform the surface of a platinum-iridium tubular workpiece from a relatively smooth, visually shiny state to a finely textured, visually matte state that may be compressed into a conductive member with a surface having an ESA to AP ratio of at least 2.0, the grit blasting process may be performed with a Crystal Mark MV-2 Micro Sandblaster and the following parameters: sodium bicarbonate #34 particles from Crystal Mark, Inc., which includes particles up to 75 μm; particle feed rate of 7 out of 10; nozzle orifice diameter of 0.032 inch; air pressure of 75 psi; working distance of 0.5 to 1.0 inch; and blasting time of about 3 seconds.

A noted above, silicone primer may be applied to the front surfaces 132 and 136 of the conductive members 120 and 126 in the area of the window frames 124 and 130, as well as to the rear surfaces 134 and 138. The present inventors have determined that some of the primer applied to the surface of the conductive members that will be aligned with the window frames 124 and 130 may enter and remain in the area that will be exposed by the windows. For example, and referring to FIGS. 16 and 17, the assembled nerve cuff 102 may include one or more contacts 112 (or 114) wherein primer 156 covers the conductive member rear surface 134 (or 138), the side surfaces, and the portion of the conductive member front surface 132 (or 136) under the window frame 124 (or 128). Additionally, a small quantity 158 of the silicone primer 156 is located on the front surface 132 (or 136) within the window 122 (or 128). Alternatively, or in addition, some of the silicone adhesive (not shown) that secures the cuff body front and rear layers 116 and 118 to one another may be present within the window 122 (or 128) on the front surface 132 (or 136). The silicone primer and/or adhesive (collectively "contaminants") within the window frame compromises the electrical performance and biocompatibility of the associated nerve cuff. Accordingly, an assembled nerve cuff may be subjected to second grit blasting process that is configured to remove any contaminants that are on the front surfaces of the conductive members within the windows without damaging the window frames or other parts of the front layer.

Figures 14, 15, 16, 17, 18, 19:
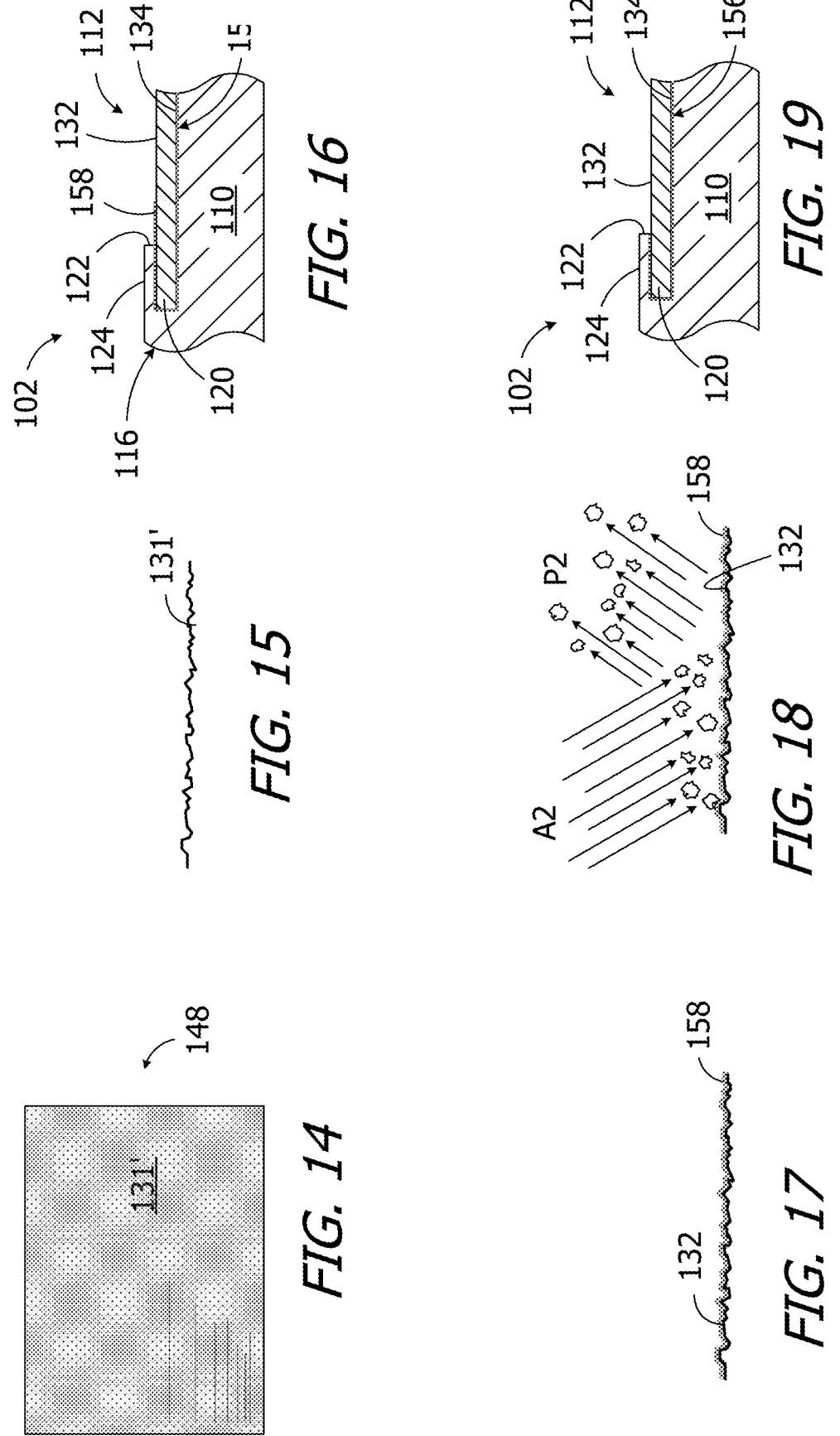
FIG. 14 is a top view of the tubular workpiece illustrated in FIG. 10 after undergoing a pre-assembly grit blasting process.
FIG. 15 is a magnified side view of the outer surface of the tubular workpiece illustrated in FIG. 10 after undergoing a pre-assembly grit blasting process.
FIG. 16 is a section view of a portion of the nerve cuff illustrated in FIG. 1 prior to undergoing a post-assembly grit blasting process.
FIG. 17 is a magnified side view of the outer surface of a conductive member of the nerve cuff illustrated in FIG. 1 prior to undergoing a post-assembly grit blasting process.
FIG. 18 is a magnified side view of the outer surface of a conductive member of the nerve cuff illustrated in FIG. 1 undergoing a post-assembly grit blasting process.
FIG. 19 is a section view of a portion of the nerve cuff illustrated in FIG. 1 after undergoing a post-assembly grit blasting process.

Referring to FIGS. 18 and 19, a second grit blasting process that involves shooting a stream of small particulates P2 at the exposed primer 158 (and/or adhesive) in a jet of air A2 may be used to clean the surface 132 (or 136) within the windows 122 (or 128). The grit blasting parameters of the second grit blasting process may be different than those of the first grit basting process. For example, the grit blasting parameters may be such that the second grit blasting process removes contaminants (e.g., primer and/or adhesive flash) from the platinum-iridium contact member surfaces without damaging the window frame 124 (or 130) and other portions of the nerve cuff. In one specific example, the grit blasting process may be performed with a Comco AccuFlo® micro-abrasive blasting machine and the following parameters: sodium bicarbonate PD1007-25 from Comco Inc., which includes particles up to 50 μm; nozzle orifice diameter of 0.030 inch; air pressure of 50 psi; working distance of 1.25 to 1.5 inch; and blasting time of about 3 seconds.

With respect to dimensions, the exemplary nerve cuffs described herein are configured to accommodate HGN structures that have diameters of about 2.5 mm (e.g., the HGN GM branch 24), about 3.0 mm (e.g., the HGN GM branch 24 in a swollen state), and about 4.0 mm (e.g., the HON trunk 22). The plurality of contacts 112-1 and plurality of contacts 112-2 which, as noted above, each function as single relatively wide contact and are sized such that the relatively wide contacts will each extend completely around the inner lumen 174 (FIG. 9) defined by the nerve cuff, i.e., 360° or more around the longitudinal axis of the inner lumen, when the cuff body 110 is in the fully furled state that accommodates an HGN structure having a diameter of about 2.5 mm, Viewed as a group, the relatively narrow contacts 114 also will extend completely around the inner lumen 174 when the when the cuff body 110 is in the fully furled state. The relatively wide pluralities of contacts 112-1 and 112-2 will also extend substantially around the inner lumen 174, i.e., at least 288° in some examples and 360° or more in other examples, around the longitudinal axis of the inner lumen, when the cuff body 110 is in an expanded and less tightly furled state that accommodates an HGN structure having a diameter of about 4.0 mm, as will, when viewed as a group, the relatively narrow contacts 114.

The dimensions of the present nerve cuffs, including the various elements thereof, may by any dimensions that result in the nerve cuffs functioning as intended. With respect to the dimensions of the cuff body 110 of the exemplary nerve cuff 102, and referring to FIG. 5, the cuff body is about 1.1 inches wide and about 034 inches long. As used herein in the context of dimensions, the word "about" means±10-20%. The width of the stimulation region 148 is about 0.6 inches, while the width of the compression region 150 is about 0.4 inches. The individual contacts 112 are same size, and the relatively narrow contacts 114 are the same size, in the illustrated implementation. In other implementations, the contacts 112 may be different sizes and/or the relatively narrow contacts 114 may be different sizes.

Figure 20:
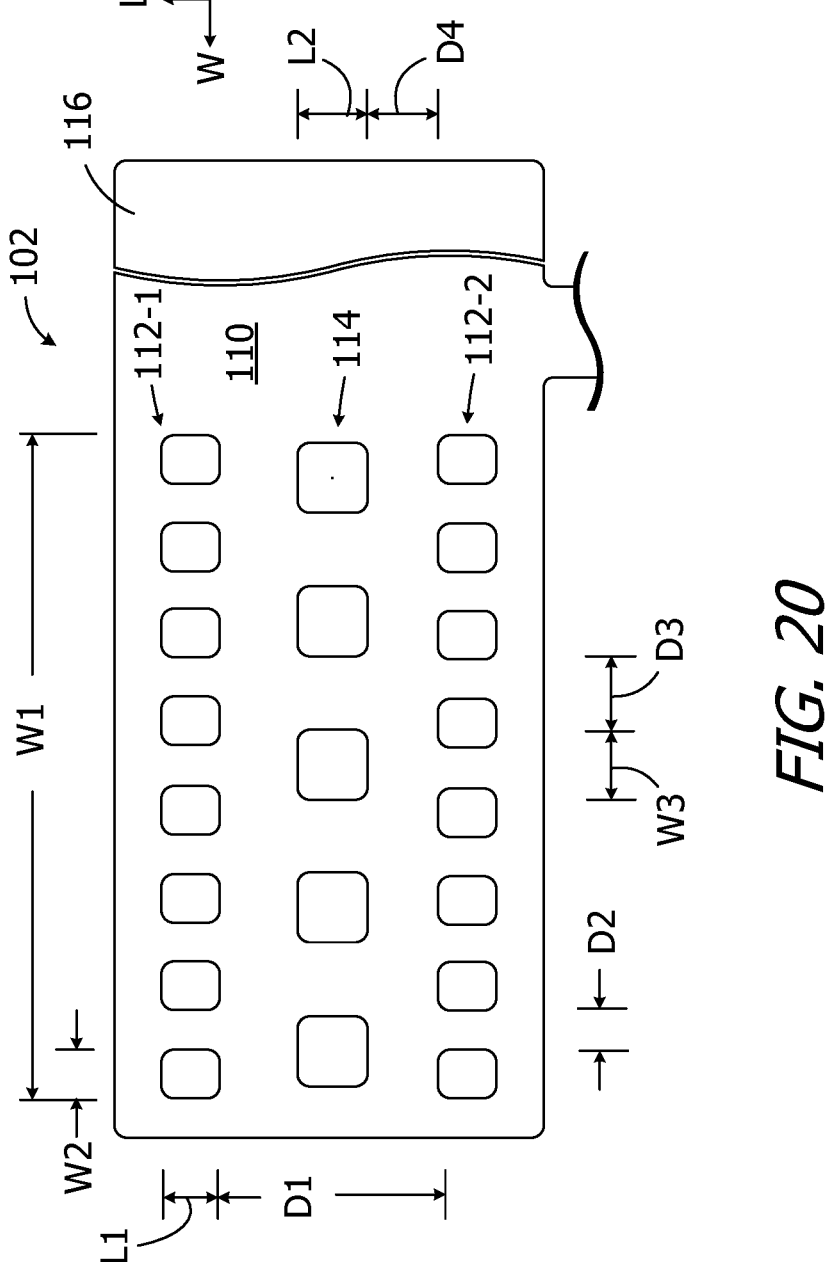
FIG. 20 is a front view of the nerve cuff illustrated in FIG. 1 in an unfurled state.

Referring to FIG. 20, the width W1 of the total width each group of contacts 112-1 and 112-2 is about 0.5 inches, the length L1 is about 0.04 inches, the width W2 is about 0.03 inches, the effective surface area is at least square inches, the distance D1 between contacts 112-1 and contacts 112-2 is about 0.2 inches, and the distance D2 between adjacent contacts 112 is about 0.02 inches. The width W3 of the contacts 114 is about 0.07 inches, the length L2 is about 0.07 inches, the effective surface area is at least 0.001 square inches, and the distance D3 between the contacts 114 is about 0.05 inches. The distance D3 may also be increased or decreased as desired to accomplish various stimulation objectives. The distance D4 between the contacts 114 and the contacts 112-1 and 112-2 is about 0.06 inches. It should be noted that the present contacts, conductive members, cuff bodies and nerve cuffs are not limited to the exemplary embodiments described above. By way of example, the sizes, shapes and spacings of the conducive members and the windows (and, therefore, the contacts) may be varied.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. A method, comprising:

forming a nerve cuff by combining a plurality of electrically conductive members with respective rear surfaces and grit blasted front surfaces, which prior to combining were formed from tubular workpieces that were grit blasted and then flattened into the electrically conductive members, with a nerve cuff body, which includes a respective plurality of windows, in such a manner that exposed portions of the grit blasted front surfaces are within the windows.

2. A method as claimed in claim 1, wherein the rear surfaces of the electrically conductive members comprise grit blasted rear surfaces.

3. A method as claimed in claim 1, wherein the cuff body includes a plurality of window frames that extend around respective windows and cover portions of the front surfaces of the electrically conductive members.

4. A method as claimed in claim 1, wherein the front surfaces of the electrically conductive members define respective outer perimeters and areas defined by the outer perimeters ("APs");

the front surfaces of the electrically conductive members define respective effective surface areas ("ESAs"); and the front surfaces of the electrically conductive members define respective ESA to AP ratios that are at least 2.0.

5. A method as claimed in claim 4, wherein the ESA to AP ratios are selected from the group consisting of at least 2.0, at least 3.0, at least 4.0, at least 5.0, at least 6.0, at least 7.0, at least 8.0, at least 9.0, and at least 10.0.

6. A method as claimed in claim 1, wherein the windows define respective perimeters and areas defined by the perimeters ("AWs");

the exposed portions of the front surfaces of the electrically conductive members define respective effective surface areas ("EPESAs"); and EPESA to AW ratios of at least 2.0 are defined at the electrically conductive members.

7. A method as claimed in claim 6, wherein the EPESA to AW ratios are selected from the group consisting of at least 2.0, at least 3.0, at least 4.0, at least 5.0, at least 6.0, at least 7.0, at least 8.0, at least 9.0, and at least 10.0.

8. A method as claimed in claim 1, further comprising:

removing primer and/or adhesive from surfaces of the electrically conductive members within the windows of the formed nerve cuff with a grit blasting process.

9. A method as claimed in claim 1, wherein the front surfaces of the electrically conductive members each define a respective average surface roughness that is at least 100 nm.

10. A method as claimed in claim 9, wherein the average surface roughness is in a range selected from the group consisting of 100 nm to 800 nm, 400 nm to 700 nm, and 500 nm to 600 nm.

11. A method, comprising:

grit blasting tubular workpieces formed from conductive material using first grit blasting parameters to form a grit blasted conductive surface on the tubular workpieces;

compressing the grit blasted tubular workpieces (148) into flat grit blasted conductive members;

assembling a nerve cuff that includes a cuff body having a plurality of windows and the flat grit basted conductive members positioned such that portions of the flat grit blasted conductive members are located within the windows; and removing contaminants from the flat grit blasted conductive member portions located within the windows of the assembled nerve cuff by grit blasting the grit blasted conductive material located within the windows using second grit blasting parameters that are different than the first grit blasting parameters.

12. A method as claimed in claim 11, wherein one of the first grit blasting parameters is sodium bicarbonate particles.

13. A method as claimed in claim 11, wherein one of the first grit blasting parameters is sodium bicarbonate particles having a first maximum size; and one of the second grit blasting parameters is sodium bicarbonate particles having a second maximum size that is less than the first maximum size.

14. A method as claimed in claim 13, wherein one of the first grit blasting parameters is a first air pressure; and one of the second grit blasting parameters a second air pressure that is less than the first air pressure.

15. A method as claimed in claim 11, wherein the contaminants comprise at least one of primer and adhesive.

16. A method as claimed in claim 11, wherein the windows define respective perimeters and areas ("AWs") defined by the perimeters;

the grit blasted conductive material located within the windows define respective effective surface areas ("EPESAs"); and EPESA to AW ratios of at least 2.0 are defined at each window.

17. A method as claimed in claim 16, wherein the EPESA to AW ratios are selected from the group consisting of at least 2.0, at least 3.0, at least 4.0, at least 5.0, at least 6.0, at least 7.0, at least 8.0, at least 9.0, and at least 10.0.

18. A method as claimed in claim 11, wherein the front surfaces of the flat grit blasted conductive members each define a respective average surface roughnesses that is at least 100 nm.

19. A method as claimed in claim 18, wherein the average surface roughness is in a range selected from the group consisting of 100 nm to 800 nm, 400 nm to 700 nm, and 500 nm to 600 nm.

* * * * *